United States Patent [19]

Hobbs et al.

[11] Patent Number: 5,234,695
[45] Date of Patent: Aug. 10, 1993

[54] WATER DISPERSIBLE VITAMIN E COMPOSITION

[75] Inventors: Howard K. Hobbs; James E. Huffaker; Eileen M. Taggart; Andreas M. Papas, all of Kingsport, Tenn.

[73] Assignee: Eastman Kodak Company, Rochester, N.Y.

[21] Appl. No.: 556,518

[22] Filed: Jul. 24, 1990

[51] Int. Cl.$^5$ ............... A61K 9/14; A61K 31/355
[52] U.S. Cl. .................. 424/489; 424/498; 424/502; 514/458; 514/770; 514/778; 514/786
[58] Field of Search ............ 424/489, 499, 502

[56] References Cited

U.S. PATENT DOCUMENTS

| 2,680,749 | 6/1954 | Cawley et al. | 260/345.5 |
| 3,639,587 | 2/1972 | Ames | 424/173 |
| 3,914,430 | 10/1975 | Cannalonga et al. | 424/284 |
| 4,262,017 | 4/1981 | Kuipers et al. | 424/284 |
| 4,711,894 | 12/1987 | Wenzel et al. | 514/458 |

FOREIGN PATENT DOCUMENTS

| 816051 | 5/1966 | Canada . |
| 87-100296 | 1/1987 | European Pat. Off. . |
| 285682 | 10/1988 | European Pat. Off. . |
| 287488 | 10/1988 | European Pat. Off. . |
| 57-181009 | 11/1982 | Japan . |
| 61-060619 | 3/1986 | Japan . |
| WO88/00045 | 1/1988 | PCT Int'l Appl. . |
| 993138 | 5/1965 | United Kingdom . |
| 1147210 | 6/1966 | United Kingdom . |

OTHER PUBLICATIONS

"Vitamin E" 8th Annual Dr. Scholl Conference on nutrition of captive wild animals (Papas et al 1989).
Eastman Products (Publication No. V-4 Oct. 1989)
"TPGS Therapy for Vitamin E Deficiency" Gastroenterology 1987:93: 975-85 (Sokol et al, Nov. 1987).
"Vitamin E and Adult Liver Disease" The American Journal of Clinical Nutrition 41:66-72 (Sokol et al, Jan. 1985).
Remingtons Pharmaceutical Sciences, Mack Publishing Co. 1988 pp. 1307, 1312.

*Primary Examiner*—Thurman K. Page
*Assistant Examiner*—James M. Spear
*Attorney, Agent, or Firm*—Mark A. Montgomery; William P. Heath, Jr.

[57] ABSTRACT

A free flowing powder is prepared containing a water-soluble vitamin E compound and at least one fatty acid ester of glycerine. The powder is prepared by blending a low viscosity mixture of the vitamin E compound and fatty acid ester followed by spraying.

13 Claims, No Drawings

WATER DISPERSIBLE VITAMIN E COMPOSITION

FIELD OF THE INVENTION

This invention relates to a water dispersible vitamin E composition and method of preparation. More particularly the present invention relates to a water dispersible powder containing water soluble vitamin E for use as a food additive.

BACKGROUND OF THE INVENTION

Vitamin E comprises a group of natural substances known as tocopherols. These are fat soluble, closely related chemical compounds commonly found in vegetation and more abundantly in seeds. d-Alpha-tocopherol has the greatest biological activity while its homologs have vitamin E activity to a lesser extent. Alpha-tocopherol in its natural state is easily absorbed and utilized in humans and animals. Processing of foods and feeds by industry for long term storage promotes accelerated degradation of effective vitamin E content. To compensate for the loss of natural vitamin E from food sources, nutritional supplements of natural or synthetic fat soluble vitamin E supplements are administered by injection or orally. However, certain human and animal species do not sufficiently absorb the natural or synthetic fat soluble vitamin E supplements.

Water-soluble tocopherol derivatives are disclosed in U.S. 2,680,749. These water soluble vitamin E derivatives are waxy compounds identified generally as alpha-tocopheryl polyethylene glycol esters. It has been demonstrated in humans with malabsorption syndromes that a water solution of these vitamin E derivatives is an excellent source of vitamin E. d-Alpha-tocopherol polyethylene glycol ester is a waxy material that is melted and added up to 20 wt % to hot water to form a slurry. This slurry must then be stirred vigorously 2 to 4 hours to form an aqueous solution. This solution of vitamin E derivative is either ingested in the liquid state or is placed on a dry carrier such as fumed silica or cellulose or placed on a dry food carrier such as milk solids. The use of a solution of this vitamin E supplement, however, has limited utility. A powdered material would be preferable due to the ease in handling, since it would not require the additional steps of forming a water solution and drying when mixed with feeds. Additionally, a powdered form of this water soluble vitamin E derivative would not require refrigeration since it would not promote microbial growth as does the water solution.

There are many methods of forming various vitamin products, including vitamin E, into a free flowing composition such as disclosed in U.S. 3,914,430 which discloses a spray drying process. However, these known methods are for the fat or lipid soluble vitamin E forms and are not applicable to the water soluble vitamin E derivative. It would, therefore, be very desirable to be able to produce a free flowing dry powdered form of alpha-tocopherol polyethylene glycol ester without the need of first forming an aqueous solution.

SUMMARY OF THE INVENTION

The composition of the present invention is a free flowing powder comprising a water soluble vitamin E compound and a material having an overall melting point of at least about 30° C., containing at least one fatty acid ester of glycerine. This composition is prepared by blending a low viscosity mixture of the water soluble vitamin E compound and the material containing at least one fatty acid ester of glycerine followed by spraying the mixture to form solid particles. The process of producing the vitamin E powder avoids the water solution step.

DETAILED DESCRIPTION OF THE INVENTION

The water dispersible vitamin E composition of the present invention more particularly comprises a free flowing powder having an average particle size between about 100 and 250 microns comprising (a) about 10 to 80 wt % of at least one water soluble vitamin E compound, and (b) a material having an overall melting point of at least 40° C. comprising at least one fatty acid ester of glycerine. The concentration of the vitamin E compound in the composition results in a final vitamin E International Units of about 40 to about 300 IU/gram.

The water soluble vitamin E compound of the present invention is preferably an alpha-tocopherol polyethylene glycol ester, more preferably d-alpha-tocopheryl polyethylene glycol 1000 succinate (TPGS). This TPGS material is a waxy compound that is represented by the formula:

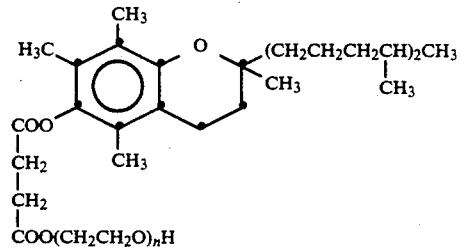

TPGS is prepared by the esterification of polyethylene glycol 1000 to the acid group of crystalline d-alpha tocopheryl acid succinate. Because vitamin E TPGS is water-soluble while other forms of vitamin E are fat-soluble, TPGS is absorbed by an entirely different mechanism. Fat-soluble vitamin E requires the use of bile salts in the gut for absorption from the intestinal lumen through to the intestinal cells. Vitamin E TPGS is absorbed without the need for bile salts activity. TPGS has the ability of transferring vitamin E into the intestinal cells with no need of assistance.

The water dispersible powder of the present invention containing vitamin E TPGS dissolves easily in water. Five grams of this powder dissolves in 200 ml of ambient water with light stirring in less than 10 minutes. This TPGS powder is clearly an improvement over TPGS alone which requires hours of stirring in hot water to be dissolved. This means that the powder can be ingested directly, such as when admixed with feed, and be dissolved and absorbed completely prior to defecation.

The material of (b) preferably has an overall melting point in the range of about 40° to 70° C. with a melting point of about 55° C. being most preferred. However, the total powdered composition, (a) plus (b), has an overall melting point between 20° and 70° C. preferably between 35° and 55° C. with a melting point of about 50° C. being most preferred.

The fatty acid ester of glycerine in the material of (b) preferably comprises a distilled mixture of mono and diglycerides having a melting point in the range of 54–70° C. These fatty acid esters of glycerine are edible fats and oils obtained from suitable fatty acid sources such as soybean oil, palm oil, lard and tallow. The source of the fat or oil is hydrogenated to an iodine value of below 5 to raise the melting point. The hydrogenated fat or oil is then reacted with glycerine in the presence of a catalyst. The reaction mixture is a mixture of monoglycerides and diglycerides. The monoglycerides are removed from the mixture by high vacuum short path distillation, i.e., molecular distillation. The fatty acid distribution of the product is the same as the source fat or oil. For example, hydrogenated soybean oil gives mainly monoglyceride stearic acid while palm oil gives a mixture of palmitic and stearic acid monoglyceride. These fatty acid esters of glycerine are preferably derived from soybean oil and contain at least 90% monoglyceride.

The material of (b) is more preferably a binary mixture comprising at least one distilled propylene glycol monoester having a melting point in the range of 32°–46° C. and a mixture of distilled mono and diglycerides having a melting point in the range of 54°–70° C. The material of (b), based on the total of (a) plus (b), preferably comprises between about 10 and 30 wt % distilled monoglyceride and between about 20 and 40 wt % propylene glycol monoester. The material of (b) more preferably comprises a mixture containing about 20 wt % distilled monoglycerides (having a diglyceride content of less than 10% and a melting point of about 70° C.) and about 30 wt % distilled propylene glycol monoester (having a melting point of about 45° C.). Any distilled monoglyceride having a melting point in the range of 54°–70° C. or any distilled propylene glycol monoester having a melting point in the range of 32°–46° C. can be used so long as the melting point of the binary mixture with TPGS is between 20 and 70° C. preferably between about 35° and 55° C.

The distilled propylene glycol monoester can be used alone with TPGS, however, this is less preferred. The distilled propylene glycol monoester is made similar to the mixture of mono and diglyceride except that a large excess of propylene glycol is used instead of glycerine and after reaction the excess propylene glycol is stripped out in a turbo film stripper then the residue separates into layers with glycerine being the bottom layer. The layers are separated and top layer containing the product is molecularly distilled to yield propylene glycol monoester.

The water dispersible vitamin E composition preferably further comprises at least one suitable flow agent. This flow agent is preferably selected from the group consisting of silicon dioxide, fumed silica, amorphous fumed silica, starch, and a synthetic amorphous precipitated silica, and is present in a concentration up to about 5 wt % based on the total of (a) plus (b). This flow agent preferably is present in a concentration of about 2 wt % and is most preferably fumed silica having an average particle size of about 0.1 micron.

The water dispersible vitamin E composition preferably comprises about 20 to 60 wt % of at least one water soluble vitamin E compound. The composition above preferably comprises between about 40 and 60 wt % of the vitamin E compound, with about 50 wt % being most preferred. The concentration of the vitamin E compound in the composition most preferably results in a final vitamin E International Units of at least 190 IU/gram.

The process of producing the free flowing vitamin E powder preferably comprises:
(A) blending a low viscosity mixture of about 40 and 60 wt % of at least one water soluble vitamin E compound and at least one fatty acid ester of glycerine; and
(B) spraying the mixture to form solid particles having an average particle size between about 100 and 250 microns.

The powder material is preferably prepared by melt blending the ingredients until a homogeneous mass is obtained and then forming a powder from the mass.

The mixture of (A) preferably has a viscosity of at least about 120 centipoise at 65° C. and step (A) is a melt blending step conducted at a temperature between about 60 and 70° C.

Step (A) preferably comprises melt blended vitamin E TPGS solid with the other ingredients maintaining each component at a temperature above their respective melting point so that each is in molten phase. These molten compounds are then thoroughly mixed to homogeneity. Alternatively, step (A) comprises mixing the materials at room temperature in powder form and then raising the temperature of the mixture at least to the melting point of ingredient that melts at the highest temperature followed by thorough blending. After blending the mixture can be powdered by conventional means such as spray chilling or alternatively freezing and pulverizing, etc. However, step (B) is preferably a spray chilling process conducted at a temperature between about 10° and 15° C. The molten mixture of (A) is preferably pumped to the top of a tower and sprayed through nozzles to cool atmosphere causing solidification of the product into small particle sizes.

The process further preferably comprises a step between steps (A) and (B) of cooling the mixture of (A) into a temperature between about 15° and 20° C. Process step (A) is preferably conducted in a stainless steel tank with a paddle agitator while Step (B) is preferably conducted in a spray chiller.

The flow agent is preferably added during spray chilling but can be added after the powder is manufactured.

The following examples are included to illustrate the present invention but are not intended to limit the reasonable scope thereof.

EXAMPLES

Example 1

This example illustrates the water dispersibility of the composition of the present invention. A mixture was prepared containing 75 grams (49.5 wt %) of vitamin E (d-alpha tocopheryl polyethylene glycol 1000 succinate (TPGS) from Eastman Chemical Company (ECC) and 75 grams (49.5 wt %) of a food emulsifier from ECC. The emulsifier contained 51 wt % of a distilled propylene glycol monoester having a 90% minimum monoester content, a melting point of approximately 45° C. (113° F.) and an iodine value of 5 maximum, prepared from fully hydrogenated soybean oil; 37 wt % distilled monoglycerides having a 90% minimum monoester content, a melting point of 69° C. (156° F.) and an iodine value of 5 maximum, prepared from fully hydrogenated soybean oil; and 12% sodium stearoyl lactylate. The mixture was heated to approximately 69° C. (156° F.) and mixed to homogeneity. The mixture was poured onto a flat tray and allowed to cool to room temperature. The mixture was then placed in a freezer for 30 minutes at 0° C. The chilled mixture was combined with 50 grams of dry ice and pulverized in a Waring blender for 1 minute. The powder was weighed out and 1 wt % Sylox 15 (micronsized silica from Davison Chemical Company) was added as flow agent.

The resulting powder was tested for hydration characteristics by stirring 10 grams of the powder into a beaker containing 200 grams of ambient water. The powder dispersed in water rapidly i.e. less than 2 minutes of hand stirring.

Example 2

This example illustrates the dispersibility of the composition of the present invention in ambient water, without the use of the sodium lactylate from first example. Sodium stearoyl lactylate was excluded due to the fact that it is not approved for use in many countries.

This sample was prepared according to Example 1 except that the mixture contained 200 grams (48.75 wt %) of vitamin E (TPGS from ECC) with 114 grams (27.79 wt % based on total) of the distilled propylene glycol monoester (PGME) of Example 1, and 86 grams (20.96 wt % based on total) of the distilled monoglycerides (DMG) of Example 1. The mixture was powdered using 100 grams dry ice. Sylox 15 at 2.5 wt % was added as flow agent.

The resulting powder was tested for hydration characteristics by stirring 10 grams of the powder into a beaker containing 200 grams of ambient water. The resultant product dissolved in ambient water immediately upon stirring. The product was a free flowing, non-compacting powder that had a melting point of 53° C. (127° F.). This powder is preferred due to its ease of manufacture and most desired flowability characteristics. The powder is also preferred due to its hydrating ability as determined by subjective mouth feel testing.

Example 3

This example illustrates the difference between the hydration of a binary combination of TPGS and distilled monoglycerides and the preferred ternary combination shown in Example 2.

This sample was prepared as described in previous Examples 1 and 2 except that the mixture contained 200 grams (49.0 wt %) vitamin E (TPGS from ECC) and 200 grams (49.0 wt %) DMG. Sylox 15 was added at a level of 2.5%. The melting point of this test powder was 65° C. (149° F.).

The resulting powder was tested for hydration characteristics by stirring 10 grams of the powder into a beaker containing 200 grams of ambient water. The powder dispersed in ambient water with 10 min. of hand stirring. Mouth feel demonstrated a delay in hydration as tacky feel remained on tongue after ingestion.

Although this powder displayed acceptable release characteristics, the lack of P-06 produced a powder that is harder than that prepared in Example 2 and does not dissolve as easily as Example 2. Therefore, the powder prepared in Example 2 illustrates the preferred formulation.

Example 4

New formulations were prepared according to Example 1 but varying the concentration of each of the components, in order to determine the ideal candidate for optimum powder formation. Swellability (% weight increase) was determined on several formulation examples. The procedure involved drying the powder for 7 days, until no change in weights were observed. The samples were then placed in a closed chamber for 354 hours at 79.5% humidity. These results are presented in the following table.

TABLE 1

| # | Formulation % | | | | Melting Point | % Weight Increase 354 Hours |
|---|---|---|---|---|---|---|
| | TPGS | PGME | DMG | Sylox 15 | | |
| 1 | 48.75 | 27.79 | 20.96* | 2.5 | 53° C. | 1.64 |
| 2 | 49.0 | — | 49.0** | 2.0 | 65° C. | N.D. |
| 3 | 48.25 | 48.25 | — | 3.5 | 34° C. | N.D. |
| 4 | 48.75 | 39.0 | 9.75 | 2.5 | 41° C. | 1.67 |
| 5 | 48.75 | 29.25 | 19.50 | 2.5 | 46° C. | 1.63 |
| 6 | 48.75 | 19.50 | 29.25 | 2.5 | 52° C. | 1.50 |
| 7 | 48.75 | 9.75 | 39.0 | 2.5 | 57° C. | 1.38 |

*Formulation of Example 2
**Formulation of Example 3
N.D. Swellability not determined due to excessive hardness or excessive softness of the experimental powder.

Formulations listed in Table 1 as 1, 4, 5, 6 and 7 all display acceptable release profiles as determined by swellability. Sample 1 (Example 2) is preferred due to manufacturing concerns and superior flowability.

Example 5

This example shows that some animals are not able to effectively use fat-soluble forms of vitamin E. In these animals a water-soluble form is required. Examples of such animals are elephants and black rhinoceros. The following trial was conducted with two captive female Asian elephants named Candy (estimated age 34 years, weight 3264 kilos) and Mimi (estimated age 31 years, weight 4855 kilograms). During the trial they continued to receive the same diet as for the previous 9 months such that any change in their blood vitamin E (measured as alpha-tocopherol in the blood serum or plasma) would reflect absorption of supplemental vitamin E in the diet (as described in: vitamin E a Comprehensive Treatise, Machlin, L. Ed., Marcel Dekker, Inc. New York, 1980).

These animals were supplemented with the following fat soluble forms of vitamin E: d-alpha-tocopherol (ECC vitamin E 5-67) at 5.1 International Units/kilogram of body weight (IU/kg) or at 10.2 IU/kg; and d-α-tocopheryl acetate (ECC vitamin E 6-100) at 30 IU/kg. Supplementation was by mixing the intended dose with a part of their diet in order to assure full consumption. These levels of supplementation are high and if absorbed they would produce a substantial increase of the serum α-tocopherol over the no supplementation period. Blood was drawn from an ear vein and allowed to stand in a dark area 30–60 minutes for clotting to occur. After centrifugation for 10 minutes at 3,300 revolutions per minute serum was separated and stored at −77° C. The serum was analyzed for alpha-tocopherol by the method described by L. J. Hatam and H. J. Kayden (Journal of Lipid Research vol. 20, pages 639–645, 1979). The results in Table 3 show that there was little or no change in the serum alpha-tocopherol indicating very poor absorption of the fat soluble forms of vitamin E by these animals and thus very inefficient utilization.

TABLE 3

| Day of Dosing | Vitamin E Form | Serum Alpha-Tocopherol Micrograms/Milliliter (mcg/mL) | | | |
|---|---|---|---|---|---|
| | | Candy | Mimi | Mean | Std Error |
| 1 | No supplementation | 0.23 | 0.10 | 0.17 | 0.07 |
| 2 | TOH, 5.1 IU/KG/Day | 0.23 | 0.12 | 0.17 | 0.06 |
| 3 | TOH, 5.1 IU/KG/Day | 0.20 | 0.12 | 0.16 | 0.04 |
| 4 | TOH, 5.1 IU/KG/Day | 0.23 | 0.10 | 0.17 | 0.06 |
| 5 | TOH, 5.1 IU/KG/Day | 0.22 | 0.11 | 0.16 | 0.05 |
| 7 | No supplementation | 0.19 | 0.10 | 0.15 | 0.04 |
| 11 | TOH, 10.2 IU/KG/Day | 0.19 | 0.10 | 0.14 | 0.05 |
| 15 | TOH, 10.2 IU/KG/Day | 0.21 | 0.11 | 0.16 | 0.05 |
| 18 | TOH, 10.2 IU/KG/Day | 0.21 | 0.12 | 0.17 | 0.05 |
| 22 | TOH, 10.2 IU/KG/Day | 0.17 | 0.12 | 0.15 | 0.03 |
| 25 | TOH, 10.2 IU/KG/Day | 0.16 | 0.10 | 0.13 | 0.03 |
| 29 | TOH, 10.2 IU/KG/Day | 0.17 | 0.11 | 0.14 | 0.03 |
| 32 | TOH, 10.2 IU/KG/Day | 0.13 | 0.11 | 0.12 | 0.01 |
| 36 | No supplementation | 0.16 | 0.10 | 0.13 | 0.03 |
| 39 | No supplementation | 0.22 | 0.11 | 0.16 | 0.05 |
| 42 | TAc, 30 IU/KG/Day | 0.20 | 0.12 | 0.16 | 0.04 |
| 44 | TAc, 30 IU/KG/Day | 0.16 | 0.12 | 0.14 | 0.02 |
| 45 | TAc, 30 IU/KG/Day | 0.17 | 0.10 | 0.13 | 0.03 |
| 46 | TAc, 30 IU/KG/Day | 0.18 | 0.11 | 0.15 | 0.04 |
| 47 | TAc, 30 IU/KG/Day | 0.21 | 0.11 | 0.16 | 0.05 |

TOH = d-α-Tocopherol
TAc = d-α-Tocopheryl Acetate

Example 6

This example shows that water dispersible forms manufactured from fat soluble vitamin E are not used efficiently by some animal species. In this trail two black rhinoceros were dosed with vitamin E 700 (obtained from Eastman Chemical Company), a water dispersible form prepared by embedding the d-α-tocopheryl acetate in gelatin. The vitamin E was provided in a mixture with grain and water to formulate a moist ball and was hand fed to assure consumption of the intended amount. Blood was drawn 1-2 times weekly from the radial vein on the medial surface of the forelimb. After drawn into a syringe, blood was transferred into a tube containing ethylene diamine tetraacetic acid as anticoagulant and plasma was separated by centrifugation at 3,500 revolutions per minute for 15 minutes as stored at −70° C. until analyzed for alpha-tocopherol as described above. The results in Table 4 show that despite supplementation at very high levels (1.5 and 23 IU/KG) the observed increase in the plasma concentration of alpha-tocopherol was very small indicating very poor absorption of this water dispersible form.

TABLE 4

| Week | Water Dispersible Form & Dose | Plasma Concentration in Micrograms/mL | | | |
|---|---|---|---|---|---|
| | | Rhino 110 | Rhino 108 | Mean | Std Error |
| 1 | No Supplementation | 0.10 | 0.22 | 0.16 | 0.06 |
| 2 | d-α-Tocopheryl Acetate, 1.5 IU/KG/Day | 0.11 | 0.21 | 0.16 | 0.05 |
| 3 | d-α-Tocopheryl Acetate, 1.5 IU/KG/Day | 0.13 | 0.28 | 0.21 | 0.07 |
| 4 | d-α-Tocopheryl Acetate, 1.5 IU/KG/Day | 0.10 | 0.32 | 0.21 | 0.11 |
| 5 | d-α-Tocopheryl Acetate, 23 IU/KG/Day | 0.33 | 0.37 | 0.35 | 0.02 |

Example 7

This example shows that a water soluble form of vitamin E is utilized by elephants very effectively. In this trial one Asian elephant named Dolly (age 25 years; weight 2895 kg) and three African elephants (name, sex, age and weight were respectively: Mac, male, 5, 811; Ginny, female, 3, 650; Mary, female, 3, 547) were dosed with TPGS (d-α-tocopheryl polyethylene glycol 1000 succinate) a water-soluble form of vitamin E available from Eastern Chemical Company. This vitamin E is a waxy solid and, in order to achieve proper dosing it was dissolved in hot water in a concentration of 20% by weight. The 4 elephants were doses in the amount shown in the table below by adding a proper volume onto their feed. The results show a rapid and substantial increase in the serum alpha-tocopherol concentration indicating very good adsorption of TPGS. Compared with previous examples, TPGS at considerably lower doses produced a larger increase in the blood concentration showing dramatically better effectiveness of this water soluble form.

TABLE 5

| Week | Vitamin E Form & Dose | Serum Alpha-Tocopherol, mcg/mL | | | | | |
|---|---|---|---|---|---|---|---|
| | | Dolly | Mac | Ginny | Mary | Mean | Std Error |
| 1 | No Supplementation | 0.15 | 0.11 | 0.19 | 0.11 | 0.14 | 0.02 |
| 2 | TPGS, 6.6 IU/KG/Day | 0.75 | 0.36 | 0.52 | 0.66 | 0.57 | 0.08 |
| 3 | TPGS, 6.6 IU/KG/Day | 1.27 | 0.44 | 0.49 | 0.83 | 0.76 | 0.19 |
| 4 | TPGS, 6.6 IU/KG/Day | 1.62 | 0.56 | 0.60 | 1.10 | 0.97 | 0.25 |

Example 8

This example shows that TPGS formulated according to the present invention, to provide a free flowing powder suitable for routine incorporation in the feed, was at least as effective as the liquid form in the previous example, by providing increased blood concentration of vitamin E. Three of the same elephants as in the previous example, namely Mac, Ginny and Mary were dosed with equivalent amounts of TPGS powder prepared according to Example 2. This formulated TPGS powder was added to their diet instead of the liquid. All other procedures were similar. As shown in the results below, the increase in the blood concentration was not significantly different from that observed with the liquid form indicating that the powder form is as bioavailable as the liquid form.

TABLE 6

| Week | Vitamin E Form & Dose | Plasma Alpha-Tocopherol, mcg/mL | | | |
|---|---|---|---|---|---|
| | | Mac | Ginny | Mary | Mean |
| 1 | No Supplementation | 0.19 | 0.27 | 0.31 | 0.26 |
| 2 | TPGS, 6.6 IU/KG/DAY | 0.43 | 0.53 | 0.83 | 0.60 |
| 3 | TPGS, 6.6 IU/KG/DAY | 0.71 | 0.92 | 1.26 | 0.96 |
| 4 | TPGS, 6.6 IU/KG/DAY | 0.75 | 1.02 | 1.26 | 1.01 |

We claim:

1. A water-dispersible vitamin E composition comprising a free flowing powder containing (a) about 10 to 80 wt % of at least one water soluble vitamin E compound, wherein said Vitamin E compound is an alpha-tocopheryl polyethylene glycol ester and (b) a material having an overall melting point of at least 30° C. comprising at least one fatty acid ester of glycerine.

2. The composition according to claim 1 further comprising up to about 5 wt % of at least one flow agent selected from silicon dioxide, starch, amorphous fumed silica, synthetic amorphous precipitated silica, and fumed silica.

3. The composition according to claim 2 wherein said flow agent is fumed silica having an average particle size of about 0.1 microns and is present in a concentration of about 2 wt %.

4. The composition according to claim 1 wherein the material of (b) has a melting point between about 40° and 70° C. and is selected from distilled monoglycerides having a diglyceride content of less than 10%, distilled propylene glycol monoesters, and mixtures thereof.

5. The composition according to claim 1 wherein the water soluble vitamin E compound is a waxy vitamin E compound and the material of (b) comprises distilled propylene glycol monoester having a melting point in the range of 32°-46° C. and distilled monoglycerides having a melting point in the range of 54°-70° C. and a monoglyceride content of at least 90 wt %.

6. The composition according to claim 5 wherein the composition has a vitamin E content of at least 190 IU/gram and the material of (b) comprises between about 10 and 30 wt % distilled monoglycerides and between about 20 and 40 wt % propylene glycol monoesters based on total of (a) plus (b).

7. The composition according to claim 6 wherein the material of (b) comprises about 20 wt % distilled monoglycerides and about 30 wt % distilled propylene glycol monoesters.

8. The composition according to claim 1 wherein said water soluble vitamin E compound is d-alpha-tocopheryl polyethylene glycol 1000 succinate present in a concentration between about 40 and 60 wt %.

9. A process for producing a free flowing vitamin E powder comprising:
(A) blending a low viscosity mixture of about 40 to 60 wt % of at least one water soluble vitamin E compound, wherein said Vitamin E compound is an alpha-tocopheryl polyethylene glycol ester and at least one fatty acid ester of glycerine; and
(B) spraying the mixture to form solid particles having an average particle size between about 100 and 250 microns.

10. The process according to claim 9 wherein the mixture of Step (A) has a viscosity of about 120 centipoise at 65° C. and Step (A) is a melt blending step conducted at a temperature between about 60° and 70° C.

11. The process according to claim 9 wherein Step (B) is a spray chilling step conducted at a temperature between about 10° and 15° C.

12. The process according to claim 9 further comprising the step between Steps (A) and (B) of cooling the mixture of (A) to a temperature between about 15° and 20° C.

13. The process according to claim 9 wherein Step (A) is conducted in a stainless steel tank with paddle agitator and Step (B) is conducted in a spray chiller.

* * * * *